United States Patent [19]

Miki et al.

[11] Patent Number: 4,835,325
[45] Date of Patent: May 30, 1989

[54] PROCESS FOR PRODUCING HYDROXYBENZENES

[75] Inventors: Hisaya Miki; Shintarou Araki, both of Yamaguchi; Masatoshi Nitabaru, Hiroshima, all of Japan

[73] Assignee: Mitsui Petrochemical Industries, Ltd., Tokyo, Japan

[21] Appl. No.: 173,608

[22] Filed: Mar. 25, 1988

[30] Foreign Application Priority Data

Mar. 27, 1987 [JP] Japan ................................. 62-71765

[51] Int. Cl.$^4$ ............................................. C07C 37/60
[52] U.S. Cl. ................................... 568/771; 568/741; 568/803
[58] Field of Search ............... 568/803, 771, 741, 768, 568/800

[56] References Cited

U.S. PATENT DOCUMENTS

| 2,644,014 | 6/1953 | Saunders | 568/803 |
|---|---|---|---|
| 4,434,305 | 2/1984 | Kurosaka et al. | 568/768 |
| 4,469,899 | 9/1984 | Nakamura et al. | 568/768 |
| 4,628,126 | 12/1986 | Drauz et al. | 568/803 |

FOREIGN PATENT DOCUMENTS

| 0028931 | 5/1981 | European Pat. Off. | 567/768 |
|---|---|---|---|
| 1493977 | 8/1969 | Fed. Rep. of Germany | 568/768 |
| 2325652 | 12/1973 | Fed. Rep. of Germany | 568/768 |
| 2441744 | 12/1975 | Fed. Rep. of Germany | 568/768 |
| 043942 | 11/1974 | Japan | 568/803 |
| 57-31778 | 9/1983 | Japan | 568/771 |
| 5197680 | 11/1983 | Japan | 568/771 |
| 60-149538 | 8/1985 | Japan | 568/771 |
| 60-123819 | 12/1986 | Japan | 568/771 |
| 60209275 | 3/1987 | Japan | 568/771 |

OTHER PUBLICATIONS

Patents Abstracts of Japan, vol. 11, No. 141.
Patent Abstracts of Japan, vol. 8, No. 266.
Patent Abstracts of Japan, vol. 7, No. 268.

Primary Examiner—Werren B. Lone
Attorney, Agent, or Firm—Nixon & Vanderhye

[57] ABSTRACT

Hydroxybenzenes can be produced in high yield through a one-step reaction by subjecting (a) an $\alpha,\alpha$-dialkyl-$\alpha$-hydroxymethyl group containing benzene and/or (b) a benzene containing both $\alpha,\alpha$-dialkyl-$\alpha$-hydroxymethyl and $\alpha,\alpha$-dialkyl-$\alpha$-hydroperoxymethyl groups to reaction in the presence of a nitrile, an acid and hydrogen peroxide. In a preferred mode, the reaction system further contains (c) an $\alpha,\alpha$-dialkyl-$\alpha$-hydroperoxymethyl group containing benzene.

4 Claims, No Drawings

1

PROCESS FOR PRODUCING HYDROXYBENZENES

BACKGROUND OF THE INVENTION

The present invention relates to a process for producing hydroxybenzenes such as resorcinol from (a) α, α-di-alkyl-α-hydroxymethyl group containing benzenes such as m-diisopropylbenzenedicarbinol and/or (b) benzenes containing both α, α-dialkyl-α-hydroxymethyl and α, α-dialkyl-α-hydroperoxymethyl groups, such as m-diisopropylbenzenemonocarbinol monohydro-peroxide.

A well known method for producing hydroxybenzenes such as resorcinol consists of oxidizing m-diisopropylbenzene (m-DIPB) with molecular oxygen in the presence of a base to obtain m-diisopropylbenzene dihydroperoxide (m-DHP), then decomposing m-DHP with an acid to yield resorcinol. Besides m-DHP, this method gives rise to by-product carbinols such as m-diisopropylbenzenemonocarbinol monohydroperoxide (m-HHP) and m-diisopropylbenzenedicarbinol(m-DC). Therefore, for commercial processes of resorcinol production by oxidation of m-DIPB followed by decomposition of m-DHP with an acid, it has been proposed that the by-product carbinols be reoxidized with hydrogen peroxide to form m-DHP, which may then be decomposed into resorcinol with an acid (see, for example, Japanese Patent Publication No. 52972/1983).

In this prior art process, a mixture of oxidation products containing carbinols in addition to the hydroperoxide obtained by oxidizing m-DIPB with molecular oxygen is first oxidized with hydrogen peroxide in the presence of an acid such as sulfuric acid and an aromatic hydrocarbon solvent such as toluene or a ketone solvent such as methyl isobutyl ketone, thereby reoxidizing the carbinols to form concentrated m-DHP, and in the next step, the m-DHP of increased concentration is decomposed into resorcinol with an acid. This prior art process depends on a two-stage reaction since it is difficult to achieve both reoxidation with hydrogen peroxide and decomposition with an acid simultaneously in a single step. Moreover, the two-stage reaction involves complicated procedures and results in a costly process. In addition, the yield of resorcinol produced by this method is not necessarily high.

Japanese Patent Application (OPI) No. 282333/1986 (the term "OPI" as used herein means an unexamined published Japanese patent application) discloses a one-step process for the production of 2, 6-dihydroxynaphthalene (2, 6-DHN) in which 2, 6-diisopropylnaphthalene dicarbinol is oxidized with hydrogen peroxide and acid-decomposed in acetonitrile or dioxane in the presence of an inorganic acid. Japanese Patent Application No. 209275/1985 also shows a process for 2, 6-DHN production and teaches that if a solution of the oxidation product of 2, 6-diisopropylnaphthalene (2, 6-DIPN) dissolved in ketone or toluene is subjected to oxidation and decomposition with H$_2$O$_2$ in the presence of an acid, 2, 6-DHN can be obtained in high yield by a one-step reaction without using two-stage reaction. The process disclosed in Japanese Patent Application (OPI) No. 282333/1986 shows that a satisfactory yield of 2, 6-DHN can be produced from the pure dicarbinol of 2, 6-DIPN even if the reaction is carried out in acetonitrile or dioxane. Therefore, these two processes, notwithstanding the difference in the starting material employed (dicarbinol of 2, 6-DIPN in one method and the oxidation product of 2, 6-DIPN in the other), are both directed to the production of 2, 6-DHN using H$_2$O$_2$ as an oxidizer and attain their objective by an efficient one-stage reaction performed in a solvent such as ketone, aromatic hydrocarbon, acetonitrile or dioxane.

However, the starting material for the process described in Japanese Patent Application (OPI) No. 282333/1986 has a naphthalene nucleus and it is not clear whether the process can also be applied to starting materials having a benzene nucleus. The starting material to be subjected to the reaction involved in that process is a pure form of dicarbinol containing no impurities. As already pointed out, if polyalkylbenzenes such as m-diisopropylbenzene are oxidized with molecular oxygen, a variety of oxides such as dihydroperoxide, monocarbinol monohydroperoxide and dicarbinol are produced in the form of mixtures. But it is unclear whether the process disclosed in Japanese Patent Application (OPI) No. 282333/1986 is equally applicable to mixtures of oxidation products that contain hydroperoxides in addition to carbinol.

SUMMARY OF THE INVENTION

Under the circumstances described above, the present inventors conducted studies with a view to developing a one-step process by which hydroxybenzenes can be selectively produced in high yield from (a) an α, α-dialkyl-α-hydroxymethyl group containing aromatic hydrocarbon and/or (b) an aromatic hydrocarbon containing both α, α-dialkyl-α-hydroxymethyl and α, α-dialkyl-α-hydroperoxymethyl groups.

As a result, the present inventors have found that the stated object can be attained by a process in which (a) an α, α-dialkyl-α-hydroxymethyl group containing benzene and/or (b) a benzene containing both α, α-dialkyl-α-hydroxymethyl and α, α-dialkyl-α-hydroperoxymethyl groups is subjected to reaction in the presence of a nitrile, an acid and hydrogenperoxide so as to obtain desired hydroxybenzenes.

DETAILED DESCRIPTION OF THE INVENTION

In the pocess of the present invention, (a) an α, α-dialkyl-α-hydroxymethyl group containing benzene [hereinafter sometimes abbreviated as carbinol (a)] and/or (b) a benzene containing both α, α-dialkyl-α-hydroxymethyl and α, α-dialkyl-α-hydroperoxymethyl groups [this benzene is hereinafter sometimes abbreviated as carbinol hydroperoxide (b)] are employed as starting materials for the production of hydroxybenzenes.

Specific examples of carbinol (a) to be used in the present invention include: m-bis(α, α-dimethyl-α-hydroxymethyl) benzene (which is sometimes referred to as m-diisopropylbenzene dicarbinol or simply m-DC), m-isopropyl-(α, α-dimethyl-α-hydroxymethyl) benzene, m-acetyl-(α, α-dimethyl-α-hydroxymethyl) benzene, 1, 3, 5,-tris(α, α-dimethyl-α-hydroxymethyl) benzene, 1, 3-bis(α, α-dimethyl-α-hydroxymethyl)-5-isopropylbenzene, 1-(α, α-dimethyl-α-hydroxymethyl)-3, 5-diisopropylbenzene, 1-acetyl-3, 5-bis(α, α-dimethyl-α-hydroxymethyl)benzene, 3, 5-bis(α, α-dimethyl-α-hydroxymethyl) toluene, and 3-(α, α-dimethyl-α-hydroxymethyl)-5-isopropyltoluene.

Specific examples of carbinol hydroperoxide (b) to be used in the present invention include: m-(α, α-dimethyl-α-hydroxymethyl)-(α, α-dimethyl-α-hydroperoxymethyl) benzene (which is sometimes referred to as m-diisopropylbenzene monocarbinol monohydroperoxide or simply m-HHP), 1, 3-bis($\alpha$, $\alpha$-dimethyl-$\alpha$-hydroxymethyl)-5-($\alpha$, $\alpha$-dimethyl-$\alpha$-hydroperoxymethyl) benzene, 1-($\alpha$, $\alpha$-dimethyl-$\alpha$-hydroxymethyl)-3, 5-bis($\alpha$, $\alpha$-dimethyl-$\alpha$-hydroperoxymethyl) benzene, and 1-isopropyl-3-($\alpha$, $\alpha$-dimethyl-$\alpha$-hydroxymethyl)-5-($\alpha$, $\alpha$-dimethyl-$\alpha$-hydroperoxymethyl) benzene.

The specific examples of carbinol (a) and carbinol hydroperoxide (b) listed above are those having isopropyl as the alkyl group, but it should be understood that cases where those having other secondary alkyl groups such as sec-butyl are employed are also included within the scope of the present invention.

The starting material which is to be subjected to reaction in the process of the present invention for producing hydroxybenzenes may be carbinol (a) or carbinol hydroperoxide (b) taken individually, or a mixture of (a) and (b). The starting material may further contain an $\alpha$, $\alpha$-dialkyl-$\alpha$-hydroxyperoxymethyl group containing benzene (c) [which is hereinafter sometimes abbreviated as hydroperoxide (c)] as an optional component.

Specific examples of the hydroperoxide (c) include: m-bis($\alpha$, $\alpha$-dimethyl-$\alpha$-hydroperoxymethyl) benzene, m-($\alpha$, $\alpha$-dimethyl-$\alpha$-hydroperoxymethyl)-isopropylbenzene, m-($\alpha$, $\alpha$-dimethyl-$\alpha$-hydroperoxymethyl)-acetylbenzene, 1, 3, 5-tris($\alpha$, $\alpha$-dimethyl-$\alpha$-hydroperoxymethyl) benzene, 1, 3-bis($\alpha$, $\alpha$-dimethy-$\alpha$-hydroperoxymethyl)-5-isopropylbenzene, and 1,3-diisopropyl-5-($\alpha$, $\alpha$-dimethyl-$\alpha$-hydroperoxymethyl) benzene.

For the purposes of the present invention, it is convenient to use as the starting material a mixture of the products of oxidation of polyalkylbenzenes with molecular oxygen which contains cabinol (a), carbinol hydroperoxide (b) and hydroperoxide (c). Illustrative polyalkylbenzenes include cumene, cymene, sec-butylbenzene, isopropylethylbenzene, m-diisopropylbenzene, p-diisopropylbenzene, m-diethylbenzene, p-diethylbenzene, 1, 3, 5-triisopropylbenzene, 3, 5-diisopropyltoluene, m-di-sec-butylbenzene, and p-di-sec-butylbenzene. The term "molecular oxygen" means an oxygen gas, which may be diluted with an inert gas such as nitrogen. An example of such diluted gas is atmospheric air. Oxidation of polyalkylbenzenes with molecular oxygen may be performed under known conditions by supplying molecular oxygen into the reaction system, with a radical initiator and an aqueous alkali solution being employed as required. Some of the methods that can be employed to oxidize polyalkylbenzenes with molecular oxygen are described in Japanese Patent Publication No. 52972/1983, and Japanese Patent Application (OPI) Nos. 149538/1985 and 150529/1983.

Illustrative aqueous alkali solutions are those of alkalis such as sodium hydroxide, potassium hydroxide and sodium carbonate. Such aqueous solutions are generally used in amounts of about 5–70% of the reaction system. The reaction temperature and time vary with the type of the polyalkylbenzene to be oxidized and usually employed conditions are 70°–150° C. and 2–100 hr.

After the reaction of oxidation with molecular oxygen is completed, the reaction product is freed of the oil phase by oil-water separation. If desired, the oil phase may be separated from the reaction product after adding an aromatic hydrocarbon such as benzene or toluene or a solvent such as methyl isobutyl ketone into it. The solvent to be added may be a water-soluble solvent such as acetone or acetonitrile if their water miscibility can be lowered by combining them with a slightly water-soluble solvent such as benzene, toluene or methyl isobutyl ketone.

The separated oil phase contains all or at least one of cabinol (a), carbinol hydroperoxide (b) and hydroperoxide (c). As already stressed, this mixture of oxidation products can be used in the process of the present invention as the starting material for the production of hydroxybenzenes. The proportions of the components of this mixture vary with the molar ratio of oxygen that has reacted with the polyalkylbenzens by the time the oxidation reaction is terminated. Generally speaking, carbinol (a) is contained in an amount of from 0.1 to 5 parts by weight, carbinol hydroperoxide (b) from 5 to 30 parts by weight, and hydroperoxide (c) from 30 to 70 parts by weight.

According to the process of the present invention, the afore-mentioned cabinol (a) and/or carbinol hydroperoxide (b) is subjected to reaction in the presence of a nitrile, an acid and hydrogenperoxide, thereby producing a desired hydroxybenzene.

Specific examples of the nitrile that can be used include: aliphatic nitriles such as acetonitrile, propionitrile, butyronitrile and hexanonitrile; aliphatic dinitriles such as malononitrile, succinonitrile and adiponitrile; and aromatic nitriles such as benzonitrile and tolunitrile.

These nitriles, which also serve as solvents, are used in amounts that generally range from 0.5 to 100 parts by weight, preferably from 1 to 50 parts by weight, per part by weight of the sum of carbinol (a) and/or carbinol hydroperoxide (b), and hydroperoxide (c) as well if this is present at all. If the nitrile content is not less than 0.5 parts by weight, the high selectivity for the desired hydroxybenzene and high yield are achieved. There is no particular limit for the maximum amount of nitriles that can be used but from an economic viewpoint, the nitriles are desirably used in amounts not exceeding 100 parts by weight.

Specific examples of the acid that can be used in the present invention include: inorganic acids such as sulfuric acid, hydrochloric acid, phosphoric acid, perchloric acid and hydrofluoric acid; strongly acidic ion-exchange resins; solid acids such as silica gel and silica alumina; organic acids such as chloroacetic acid, methanesulfonic acid, benzenesulfonic acid and toluenesulfonic acid; hetero polyacids such as phosphotungstic acid and phosphomolybdic acid; and Lewis acids such as boron trifluoride. These acidic catalystics may be added to the reaction system either directly or after being dissolved in appropriate inert solvents that are capable of dissolving these acidic catalysts. For instance, a soluble acid such as sulfuric acid or hydrochloric acid may be used after they are dissolved or diluted in the nitriles. The amount of acidic catalyst used depends on its type and reaction conditions but it is generally used in an amount of 0.005–10 wt %, preferably 0.01–1 wt %, of the total reaction mixture.

In the process of the present invention, the reaction is generally carried out in the presence of a solvent. Specific examples of the solvent include: aromatic hydrocarbons such as benzene, toluene, xylene, ethylbenzene, isopropylbenzene, diisopropylbenzene, triisopropylbenzene and chlorobenzene; aliphatic hydrocarbons such as dichloromethane, chloroform, carbon tetrachloride, dichloroethane, hexane, heptane, octane, nonane and cyclohexane; alcohols such as methanol, ethanol, isopropanol and butanol; ethers such as diethyl ether, diisopropyl ether, dibutyl ether and dioxane; ketones such as acetone, methyl ethyl ketone (MEK), diethyl ketone, methyl isobutyl ketone (MIBK), and acetophenone; and carboxylic acids such as acetic acid and formic acid. Among these solvents, benzene, toluene, xylene, acetone and MIBK are preferred. These solvents are generally used in amounts ranging from 10 to 95 wt % of the reaction system.

The amount of hydrogen peroxide ($H_2O_2$) to be used in the process of the present invention is expressed in terms of the molar ratio of $H_2O_2$ to carbinol group, or the number of moles of $H_2O_2$ as compared to that of carbinol group, which is the abbreviation of α, α-dialkyl-α-hydroxymethyl group present in the starting material. In performing the intended reaction, $H_2O_2$ is generally used at a $H_2O_2$/carbinol group molar ratio of 0.7–2.0, preferably in the range of 1.0–1.5. If the molar ratio of $H_2O_2$ to carbinol group is 0.7 or more, by-products will not essentially occur as a result of condensation of the unreacted carbinols. If the molar ratio of $H_2O_2$ to carbinol group is 2.0 or less, the hydroxybenzene as the reaction product will not undergo a secondary reaction with excess hydrogen peroxide and the yield of the end product will not be lowered. Therefore, the molar ratio of $H_2O_2$ to carbinol group is controlled to be within the range of 0.7–2.0.

The hydrogen peroxide to be used in the present invention may originate from various sources such as liquid hydrogen peroxide, an aqueous solution of hydrogen peroxide, as well as from substances that generate hydrogen peroxide under the reaction conditions employed, such as sodium peroxide and calcium peroxide. The reaction temperature varies somewhat with the reflux temperature of the solvent used and with the pressure in the reaction system (which is usually atomspheric but may be superatmospheric as required), but it is generally within the range of 0°–100° C., preferably 20°–80° C. The reaction time is usually in the range of from about 5 minutes to about 5 hours. The reaction may be performed either batchwise or continuously.

After completion of the reaction, the catalyst (acid) used in the method of the present invention may be neutralized as required and after recovering the by-product ketone or the solvent used, the desired hydroxybenzene is isolated by either extraction or distillation, and in some instances, is purified by further purification steps such as recrystallization.

Specific examples of the hydroxybenzenes that can be isolated include: phenol, cresol, xylenol, ethylphenol, resorcinol, m-isopropylphenol, hydroquinone, p-isopropylphenol, 1, 3, 5-trihydroxybenzene (phloroglucinol), isopropyl dihydroxybenzene, diisopropyl monohydroxybenzene, 3, 5-dihydroxytoluene, and 3-isopropyl-5-hydroxytoluene.

In accordance with the process of the present invention, hydroxybenzenes can be selectively produced from cabinol (a) and/or carbinol hydroperoxide (b) in high yield and through a one-step reaction.

The following examples are provided for the purpose of further illustrating the present invention but are in no way to be taken as limiting. In the examples, the following abbreviations are used to signify several important compounds:

m-DIPB: m-diisopropylbenzene
MIBK: methyl isobutyl ketone
m-DC: m-bis(α, α-dimethyl-α-hydroxymethyl) benzene
m-DHP: m-bis(α, α-dimethyl-α-hydroperoxymethyl) benzene
m-HHP: m-bis(α, α-dimethyl-α-hydroxymethyl)(α, α-dimethyl-α-hydroperoxymethyl) benzene
m-MHP: m-isopropyl-(α, α-dimethyl-α-hydroperoxymethyl)-benzene.

EXAMPLE 1

A mixture consisting of 1,000 parts by weight of m-DIPB and 100 parts by weight of a 3 wt % aqueous solution of sodium hydroxide was oxidized at 100° C. for 22 hours with air being blown under stirring. Throughout the oxidation reaction, 1,000 parts by weight of a 5 wt % aqueous solution of sodium hydroxide was supplied intermittently so that the pH in the reaction system would be held at 8–10. After completion of the oxidation, 2,500 parts by weight of toluene was added to the reaction system and the separating aqueous alkali layer was removed. The resulting oil layer was washed with water and dehydrated under vacuum to obtain the oxidation product of m-DIPB having the composition noted in Table 1. The content of m-DC in this product was not more than 0.5 wt %.

TABLE 1

| Components | Content (wt %) |
|---|---|
| m-DHP | 25 |
| m-HHP | 8 |
| m-MHP | 5 |
| Toluene | 57 |
| Others | 5 |

A flask equipped with a stirrer, a reflux condenser, a dropping funnel and a thermometer was charged with 0.13 g of phosphotungstic acid and 24.9 g of acetonitrile, followed by heating on a hot water bath at 60° C. To the heated charge, a mixture of the oxidation product of m-DIPB in toluene (15.3 g), 60% aqueous hydrogen peroxide (0.4 g) and acetonitrile (9.3 g) was added dropwise over a period of 10 minutes and the reaction was continued for an additional 5 minutes. In Example 1, the number of moles of $H_2O_2$ per mole of the carbinol group in the mixture of oxidation products used as the starting material for reaction (i.e., molar ratio of $H_2O_2$ to carbinol group) was 1.2.

Analysis by gas chromatography conducted after the reaction showed that the resorcinol (RS) yield as expressed by $100 \times RS/(m\text{-}DHP + m\text{-}HHP)$ was 82 mol %.

EXAMPLE 2

Reaction was performed at 64°–73° C. as in Example 1 except that the solvent to be charged into the flask was replaced by 24.9 g of a mixture of acetonitrile and toluene in equal amounts. The resorcinol yield was 72 mol %.

EXAMPLE 3

The procedures of Example 1 were repeated except that the flask was charged with 75 g of acetonitrile containing 50 mg of sulfuric acid and that the reaction temperature was changed to a reflux temperature of 80°–81° C. The reaction was continued for only one minute after the dropwise addition of the mixture of the oxidation product of m-DIPB in toluene, 60% aqueous $H_2O_2$ and acetonitrile. The resorcinol yield was 80 mol %.

EXAMPLE 4

An apparatus of the same type as what was used in Example 1 was charged with 0.5 g of m-di(2-hydroxy-2-propyl) benzene (m-DC) and 40 g of an acetonitrile solution containing 0.41 g of 60% aqueous hydrogen peroxide, followed by heating on a hot water bath at 61° C. To the heated charge, 10 g of acetonitrile containing 50 mg of sulfuric acid was added at a time. The resorcinol yield was 60 mol % in 10 minutes, and 66 mol % in 1 hour.

EXAMPLES 5–8

The procedures of Example 4 were repeated by using mixtures of acetonitrile with other solvents in place of acetonitrile. The resorcinol yield attained in 1 hour in each of Examples 5–8 is indicated in Table 2 below.

TABLE 2

| Example No. | Solvent (acetonitrile/solvent = 50/50 on wt basis) | Resorcinol yield (mol %) |
|---|---|---|
| 5 | acetone | 59 |
| 6 | toluene | 51 |
| 7 | acetic acid | 62 |
| 8 | methanol | 50 |

COMPARATIVE EXAMPLES 1–7

The procedure of Example 4 were repeated using the solvents listed in Table 3 in place of acetonitrile.

TABLE 3

| Comparative Example No. | Solvent | Resorcinol yield (mol %) |
|---|---|---|
| 1 | acetone | 18 |
| 2 | toluene | 7 |
| 3 | acetic acid | 29 |
| 4 | methanol | tr. |
| 5 | 1,4-dioxane | 5 |
| 6 | ethyl acetate | 14 |
| 7 | carbon disulfide | 31 |

EXAMPLE 9

The procedures of Example 4 were repeated except that acetonitrile was changed to benzonitrile. The resorcinol yield in 1 hr was 59 mol %.

EXAMPLE 10

An apparatus of the same type as what was used in Example 1 was charged with 6.1 g of 1, 3, 5-tris ($\alpha$, $\alpha$-dimethyl-$\alpha$-hydroxymethyl) benzene, 30 g of toluene containing 4.01 g of 60% aqueous hydrogen peroxide and 102.2 g of acetonitrile, followed by heating on a hot water bath at 85° C. To the heated charge, 7.9 g of an acetonitrile solution containing 0.15 g of sulfuric acid was added at a time. The yield of phloroglucinol obtained in one hour was 56 mol %.

EXAMPLE 11

A mixture consisting of 100 parts by weight 95% pure 1, 3, 5-triisopropylbenzene (TIPB) and 10 parts by weight of 4.5 wt % sodium hydroxide in aqueous solution was oxidized at 100° C. for 30 hours by air bubbling with stirring. During the oxidation, a 4.5 wt % aqueous solution of sodium hydroxide was supplied intermittently so that the pH of the aqueous layer in the reaction system would be held at 8–10. After completion of the oxidation, 500 parts by weight of methyl isobutyl ketone was added and the aqueous layer was separated. The remaining oil layer was dehydrated by azeotropic distillation, with part of the methyl isobutyl ketone also distilled off. The product had the following composition:

| | |
|---|---|
| 1,3,5-tris($\alpha$,$\alpha$-dimethyl-$\alpha$-hydroperoxymethyl) benzene (TRHP) | 4.0 wt % |
| 1-($\alpha$,$\alpha$-dimethyl-$\alpha$-hydroxy)-3,5-bis-($\alpha$,$\alpha$-dimethyl-$\alpha$-hydroperoxymethyl)-benzene (HDHP) | 6.8 wt % |
| 1,3-bis($\alpha$,$\alpha$-dimethyl-$\alpha$-hydroxymethyl)-5-($\alpha$,$\alpha$-dimethyl-$\alpha$-hydroperoxymethyl)-benzene (DHHP) | 2.5 wt % |
| 1,3,5-tris($\alpha$,$\alpha$-dimethyl-$\alpha$-hydroxymethyl) benzene (TC) | 0.3 wt % |
| MIBK | 82.0 wt % |

An apparatus of the same type as what was used in Example 1 was charged with 0.06 g of sulfuric acid and 20.0 g of acetonitrile, followed by heating on a hot water bath at 85° C. To the heated charge, a mixture of 20.0 g of a MIBK solution of the oxidation products of 1, 3, 5-TIPB, 0.60 g of 60% aqueous $H_2O_2$, and 20.0 g of acetonitrile was added dropwise over a period of 10 minutes, and the reaction was continued for an additional 30 minutes. The phloroglucinol yield [100×phloroglucinol/(TRHP+HDHP+DHHP+TC)] was 65 mol %.

What is claimed is:

1. A process for producing a hydroxybenzene by subjecting a starting material selected from the group consisting of (a) benzene containing an $\alpha,\alpha$-dialkyl-$\alpha$-hydroxymethyl group, (b) benzene containing both $\alpha,\alpha$-dialkyl-$\alpha$-hydroxymethyl and $\alpha,\alpha$-dialkyl-$\alpha$-hydroperoxymethyl groups, and (c) a mixture of (a) and (b), to reaction in the presence of a nitrile compound selected from the group consisting of acetonitrile, benzonitrile and a mixture thereof, an acid and hydrogen peroxide 2. A process according to claim 1, wherein said nitrile compound is used in amount ranging from 0.5 to 100 parts by weight per part by weight of the total amount of said starting material.

3. A process according to claim 1, wherein said starting material further includes benzene containing an $\alpha,\alpha$-dialkyl-$\alpha$-hydroxyperoxymethyl group.

4. A process according to claim 3, wherein said nitrile compound is used in an amount ranging from 0.5 to 100 parts by weight per part by weight of the total amount of said starting material.

* * * * *